United States Patent [19]

Habara et al.

[11] Patent Number: 4,982,327

[45] Date of Patent: Jan. 1, 1991

[54] DIGITAL SCINTILLATION CAMERA SYSTEM WITH CORRECTION FOR ANALOG SCINTILLATION CAMERA SYSTEM CHARACTERISTICS

[75] Inventors: Atsushi Habara; Takashi Ichihara; Yutaka Fujiki, all of Ootawara, Japan

[73] Assignee: Kabushiki Kaisha Toshiba, Kawasaki, Japan

[21] Appl. No.: 793,767

[22] Filed: Nov. 1, 1985

[30] Foreign Application Priority Data

Nov. 2, 1984 [JP] Japan ............................ 59-230259

[51] Int. Cl.$^5$ .............................................. G06F 15/42
[52] U.S. Cl. .................... 364/413.13; 364/413.24; 378/901; 250/363.01; 250/252.1
[58] Field of Search ............... 364/414, 571, 413.13, 364/413.24, 571.01; 250/363 R, 363 S, 369, 363.01, 363.07, 363.09, 369, 252.1; 358/111; 378/4–5, 901

[56] References Cited

U.S. PATENT DOCUMENTS

| | | | |
|---|---|---|---|
| 4,181,939 | 1/1980 | Lyons | 364/414 X |
| 4,212,061 | 7/1980 | Knoll et al. | 364/414 |
| 4,223,221 | 9/1980 | Gambini et al. | 250/363 S |
| 4,228,515 | 10/1980 | Genna et al. | 364/571 |
| 4,316,257 | 2/1982 | Del Medico et al. | 250/363 R X |
| 4,323,977 | 4/1982 | Arseneau | 364/571 |
| 4,529,883 | 7/1985 | Yamakawa et al. | 250/363 S |
| 4,566,074 | 1/1986 | Nishikawa | 364/571 |
| 4,611,283 | 9/1986 | Lumelsky et al. | 364/414 |

FOREIGN PATENT DOCUMENTS 2419328 6/1975 Fed. Rep. of Germany .
2621655 1/1977 Fed. Rep. of Germany .

OTHER PUBLICATIONS

Röfo, 110,1 pp. 108–117, 1969.

*Primary Examiner*—David L. Clark
*Attorney, Agent, or Firm*—Finnegan, Henderson, Farabow, Garrett and Dunner

[57] ABSTRACT

In a digital scintillation camera system, image data representing an radioisotope distribution is detected by a scintillation camera and is then digitized and converted to a video signal. The video signal is processed in a video imager to produce a diagnostic image on a film. A count-to-grey-level converter is arranged to convert a radiation count of diagnostic image data to a grey-level. A count-to-grey-level conversion table is accessed in the converter. The conversion table includes a correction component for obtaining the same count-density characteristics of a film as in a conventional analog scintillation camera system.

5 Claims, 3 Drawing Sheets

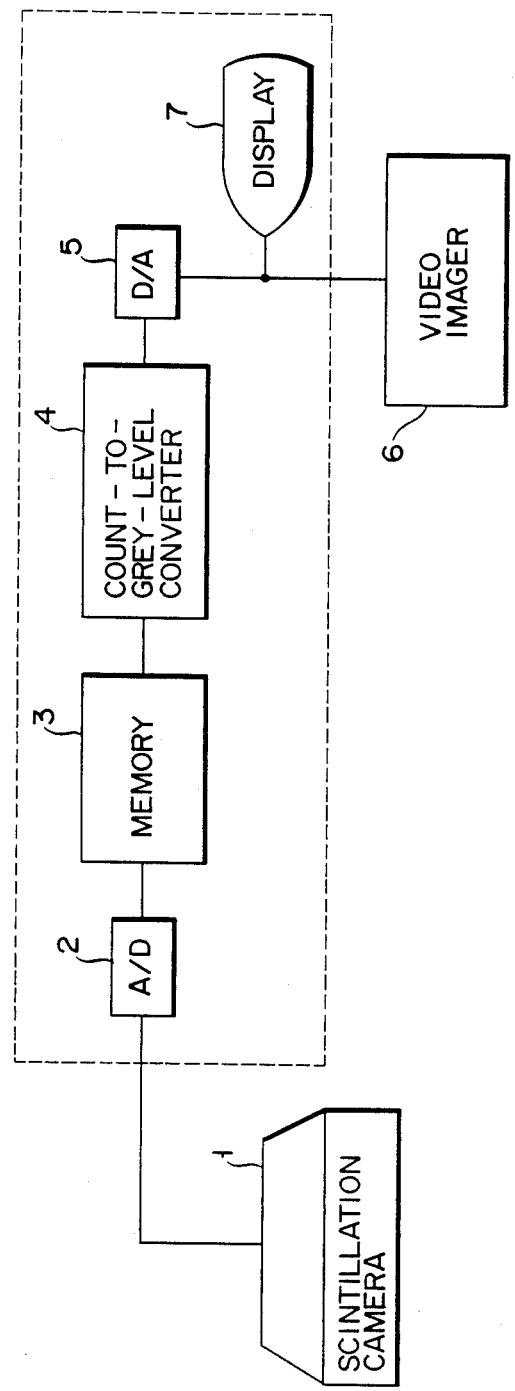
F I G. 3

DIGITAL SCINTILLATION CAMERA SYSTEM WITH CORRECTION FOR ANALOG SCINTILLATION CAMERA SYSTEM CHARACTERISTICS

BACKGROUND OF THE INVENTION

The present invention relates to a nucleus medical diagnosis system, and, more particularly, to an improvement in data processing for obtaining a preferable diagnostic image in a digital scintillation camera system.

When some radioactive drugs, i.e., drugs containing RI's (radioisotopes) are administered (e.g., injected into a blood vessel), they tend to concentrate in specific areas (e.g., a tumor or the like in an internal organ) of a patient's body. Consequently, the distribution of the drug in the patient can be externally detected through detection of the RI contained in the drug, the detected distribution being used for subsequent diagnosis.

A scintillation camera system is known as a conventional radioactive diagnosis apparatus. In the conventional scintillation camera system, a diagnostic image (i.e., an RI distribution image) of the patient is formed on a film, e.g., an X-ray film Incident positions of gamma rays sequentially emitted from an object injected with a radioactive drug are detected by the scintillation camera which then generates corresponding position signals. Light from the scintillator, upon reception of the gamma ray, is detected by a plurality of photosensors such as PMTs (photomultiplier tubes). By utilizing detection signals from the PMTs, the incident position of the gamma ray can be calculated. A gamma-ray incident position signal from the scintillation camera is supplied to the imaging apparatus of the scintillation camera (hereinafter called a "gamma imager"). The gamma imager drives a CRT (cathode-ray tube) to turn on a dot corresponding to the incident position in response to the incident position signal. The bright dot is exposed on a film such as an X-ray film. Bright dots are exposed on the film for a predetermined period of time, thereby providing an RI distribution image.

Digital scintillation camera systems have become widespread in recent years. In the conventional digital scintillation camera system, a position signal from the scintillation camera system is digitized, and a count of a pixel corresponding to an image memory is incremented in response to the position data, so that gamma-ray incident data are accumulated in the image memory. The image data stored in the memory represents RI distribution data obtained by counts representing the number of times of gamma-ray incidence for each pixel within a predetermined period of time. The image data stored in the memory is converted to a video signal representing a grey-level corresponding to the count. The video signal is displayed and supplied to a video imager. An RI distribution image from the patient is formed on a film (e.g., an X-ray film) in response to the input video signal.

The relationship between the gamma-ray count and the density of X-ray films (hereinafter called "count-density characteristics") is shown in FIG. 1. The pictures of the X-ray films were obtained by a conventional nondigital scintillation camera system (to be referred to as an analog scintillation camera system hereinafter so as to distinguish it from the digital scintillation camera system) and a digital scintillation camera system.

Referring to FIG. 1, the count is plotted along the abscissa and the density is plotted along the ordinate. As shown in FIG. 1, a characteristic curve P0 is given as a solid curve of an RI distribution image formed on an X-ray film by a gamma imager in an analog scintillation camera system, and a characteristic curve P1 is given as a broken curve of an RI distribution image formed on an X-ray film by a video imager in a digital scintillation camera system. The count-density characteristics of the analog and digital scintillation camera systems, with respect to the X-ray film, differ from each other. Therefore, even if data can be acquired under the same conditions, diagnostic images (RI distribution images) having different grey-level characteristics, i.e., density characteristics are formed on the respective X-ray films. For this reason, diagnosticians (i.e., a doctor) accustomed to a conventional analog scintillation camera system feel uneasy in operating a digital scintillation camera system. As a result, diagnosis cannot be easily performed, resulting in inconvenience.

The count-density characteristics are preferably represented by a line (count in proportion with density) different from the lines indicating characteristic curves P0 and P1, in order to allow correct display and recognition of the RI distribution. However, an image having a linear correlation between the count and the density may not be easy to recognize for an operator who is accustomed to a conventional analog scintillation camera system. Nonetheless, an image having a linear correlation between count and density is considered as the best means of expressing an RI distribution. Such an image is, in fact, expected to become the standard RI distribution image.

Count-density characteristics obtained by the digital scintillation camera system differ from those of the conventional analog scintillation camera system and from those of a system wherein a linear correlation between the count and the density is obtained. The count-density characteristics of the diagnostic image provided via the present digital scintillation camera system are, therefore, inapplicable to practical applications. Moreover, the count-density characteristics are mainly determined by exposure characteristics of the film by the video imager, and cannot be easily modified.

SUMMARY OF THE INVENTION

It is an object of the present invention to provide a digital scintillation camera system which improves image data processing, allows an operator to understand an RI distribution state and provides an easily diagnosed image.

In order to achieve the above object of the present invention, there is provided a digital scintillation camera system for converting, to a video signal image, data detected by a scintillation camera and representing a digital RI distribution, and for forming a diagnostic image, corresponding to the video signal, on a film by means of a video imager; wherein a count-to-grey-level converter is arranged to convert the radiation count of diagnostic image data into a display grey-scale data, and a count-to-grey-level conversion table, retrieved for conversion, comprises a conversion table in which is stored a correction component for obtaining predetermined count-density characteristics, thereby obtaining the desired count-density characteristics of the diagnostic image, on the film.

In the digital scintillation camera system according to the present invention, an image which allows for equivalent or easier diagnosis than that obtained by the conventional analog scintillation camera system can be obtained by using a video imager in the digital scintillation camera system.

BRIEF DESCRIPTION OF THE DRAWINGS

FIG. 3 is a block diagram showing the arrangement of a digital scintillation camera system according to an embodiment of the present invention.

DETAILED DESCRIPTION OF THE PREFERRED EMBODIMENT

The principle of the digital scintillation camera system according to the present invention will be described with reference to FIG. 2.

Figure 1:
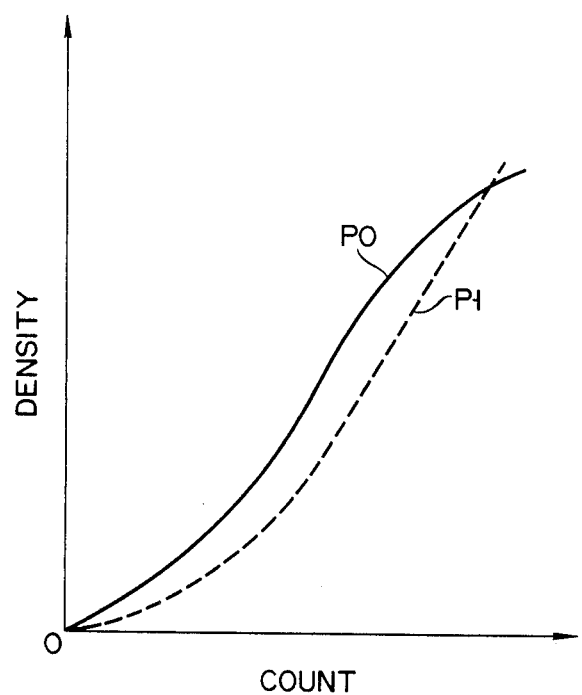
FIG. 1 is a graph showing radiation count X-ray film density characteristics obtained by conventional analog and digital scintillation camera systems.
Figure 2:
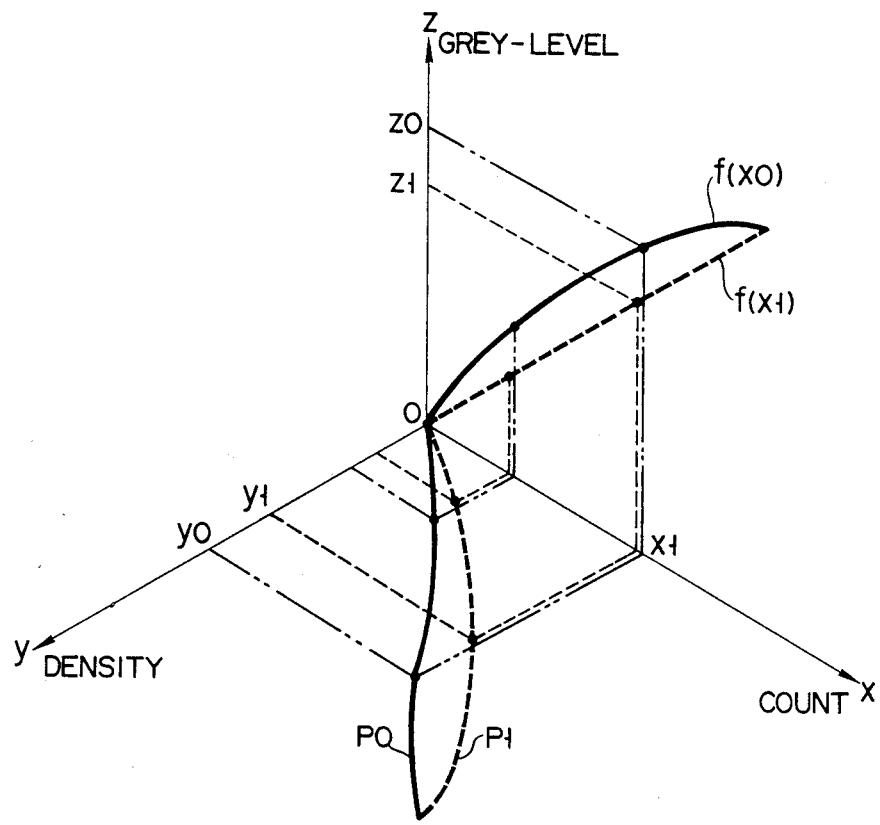
FIG. 2 is a diagram showing the principle of the present invention.

Referring to FIG. 2, x-, y- and z-axes are orthogonal to each other. A radiation (gamma ray) count is plotted along the x-axis, the density of an X-ray film is plotted along the y-axis, and a gradation, e.g., the grey-level is plotted along the z-axis. The count-density characteristics are plotted on the x-y plane, and the count vs. grey-level characteristics are plotted on the x-z plane. A characteristic curve P0, plotted on the x-y plane of FIG. 2, corresponds to the curve P0 of FIG. 1, and a characteristic curve P1, plotted on the x-y plane, corresponds to the curve P1 of FIG. 1.

The characteristic curve P1 is obtained when a function f(x) for converting, to a gradation level (i.e., a grey-level), diagnosis data stored in the image memory of the digital scintillation camera system is given as a linear function on the x-z plane, i.e., when $f(x) = f(xl)$.

The density given by the curve P1 for a given count (e.g., xl) differs from that given by the curve P0 for the given count (more specifically, the density given by the curve P1 is y1, and the density given by the curve P0 is y0, so that $y0 > y1$).

This difference exists for the following reason. In a digital scintillation camera system, digital diagnosis data is generally converted to an analog electrical signal and then a video signal. A bright dot represented by the video data is exposed by the video imager onto an X-ray film. In contrast, a gamma imager in an analog scintillation camera system does not require conversion of the analog signal to the video signal, thereby decreasing loss of the diagnostic image data.

When a diagnostic image is formed by a video imager on an X-ray film in a digital scintillation camera system, the count vs. grey-level characteristics are increased by a function f(x0) for compensating the image data stored in the image memory by a difference of the count-density characteristics of the images obtained by the analog and digital scintillation camera systems. In this state, when grey-level conversion is performed in accordance with the function f(x0), the same diagnostic image as obtained by the gamma imager of the conventional analog system can be formed.

For example, assume that a grey-level z1 is given by a function f(xl) for converting the count-to-grey-level in correspondence with a count x1 and a density y1. By adapting a conversion function f(x0) for achieving the grey-level of z0 ($z0 > z1$) for the count x1, the density of the X-ray film, with an image formed by the video imager, can be equal to that with an image formed by the gamma imager.

FIG. 3 shows a digital scintillation camera system for achieving the principle of the present invention, according to a first embodiment thereof.

Referring to FIG. 3, every time a gamma ray emitted from an RI contained in a radioactive drug administered to a patient is detected by a scintillation camera 1, the camera 1 detects an analog detection signal including a position signal representing the detected gammaray position. An analog signal from the camera 1 is digitized by an analog-to-digital (A/D) converter 2. The digital signal is supplied to a memory 3 in real time. At least one-frame digital image data of the gamma-ray count data (for a predetermined data acquisition period) for every pixel corresponding to the gamma-ray detection position is stored in the memory 3. Every time the gamma-ray detection signal is supplied from the camera 1 to the memory 3 through the A/D converter 2, the count data of the pixel corresponding to the position signal is incremented. By repeating the above operation for a predetermined period of time, the detected data for the predetermined period are accumulated to constitute diagnostic image data. A count-to-grey-level converter 4 comprises a count-to-grey-level conversion table corresponding to the function f(x0). The count-to-grey-level conversion table in the converter 4 is accessed for the diagnostic data read out from the memory 3. The diagnostic data is converted to a grey-level in accordance with the function f(x0). An output from the converter 4 is converted by a digital-to-analog (D/A) converter 5. The analog signal from the converter 5 is supplied as a video signal to a video imager 6.

The video signal from the D/A converter 5 is also supplied to a display 7, and an RI distribution image, as the diagnostic image, is displayed on the screen of the display 7.

The diagnostic image data is read out from the memory 3 in accordance with a predetermined scanning system. The readout diagnostic image data is converted by the converter 4 and then the converter 5. Therefore, the video signal can be obtained by the predetermined scanning system.

The imager 6 forms the RI distribution image, as the diagnostic image, on the X-ray film by using the video signal obtained by converting the count of the diagnostic data to the grey-level.

According to the digital scintillation camera system having the arrangement described above, the difference between the count-density characteristics of an X-ray film with an image formed by a video imager in a digital scintillation camera and the count-density characteristics of an image formed by a gamma imager in an analog scintillation camera system can be corrected by using a predetermined function f(x0) upon count-to-grey-level conversion of the diagnostic data. Therefore, the same density as that of an X-ray film with an image formed by an analog scintillation camera system can be obtained.

When, therefore, the function f(x) for correcting the difference between the count-density characteristics of an X-ray film with an image formed by a video imager and the count-density characteristics representing a linear correlation between the count and film density is used for diagnostic data count-to-grey-level conversion, a digital scintillation camera system can provide an ideal diagnostic image having an X-ray film density linearly proportional to the count.

A further improved scintillation camera system can also be provided via the following modifications. The count-to-grey-level conversion table in the converter 4 can be programable under the control of a CPU, such that a table corresponding to a desired conversion function f(x) can be selected. In this case, the same image as in the conventional analog scintillation camera system, and an image having a linear correlation between the count and the film density, can be arbitrarily selected by a user (i.e., a doctor).

Another modification may be given as follows. Standard count data is converted to a grey-level in accordance with the linear count-to-grey-level conversion characteristics, and the converted grey-level is reproduced by the imager 6 on a film. Actual, measured data is supplied to a data processor (not shown). The count-to-grey-level conversion table is corrected in accordance with the sensitivity characteristics or the like of the film. In addition, desired count-density characteristic data can be supplied to the data processor, and the count-to-grey-level conversion table can be corrected in accordance with the characteristics, thereby obtaining the desired count-density characteristic data.

What is claimed is:

1. A digital scintillation camera system for altering the actual radiation count-density characteristics of a film of a diagnostic image formed by a video imager to produce said image on a film with preselected count-density characteristics comprising:
   a scintillation camera for two-dimensionally detecting a radiation generation position, and for generating a detection signal including detection position data;
   image memory means for storing said detection signal generated by said scintillation camera, said detection signal being stored as digital image data representing radiation count data acquired for a pixel corresponding to the radiation detection position within a predetermined period of time;
   count-to-grey-level converting means for converting a count of the image data stored in said memory means to a grey-level;
   a video imager for producing said image on a film based on a video signal representing the grey-level obtained by said count-to-grey-level converting means;
   said count-to-grey-level converting means including a correction function for changing the count-to-grey-level conversion of the image data by the difference between said actual radiation count-density characteristics of the film of a diagnostic image formed by said video imager and said preselected count-density characteristics of the film.

2. A system according to claim 1, wherein said count-to-grey-level converting means includes a count-to-grey-level conversion table for storing grey-level data in association with the count data, and comprises means accessed to convert the count to the grey-level.

3. A system according to claim 1, wherein said preselected count-density characteristics are count-density characteristics of said image formed by an analog scintillation camera system.

4. A system according to claim 1, wherein said preselected count-density characteristics are such that the film density is linearly proportional to the count.

5. A digital scintillation camera system comprising:
   a scintillation camera for two-dimensionally detecting a radiation generation position, and for generating a detection signal including detection position data;
   analog-to-digital converter means for converting said detection signal into a digital signal;
   image memory means for storing said digital signal as digital image data representing radiation count data acquired for a pixel corresponding to the radiation detection position within a predetermined period of time;
   count-to-grey-level converting means for converting said count data stored in said memory means to a grey-level; and
   a video imager for producing an image on said film having count-density characteristics substantially equal to those of an image produced by bright dots exposed on a film in response to an analog position signal in an analog scintillation camera in response to a video signal incorporated with the grey-level generated by said count-to-grey-level converting means.

* * * * *